US008778838B2

(12) United States Patent
Krapp et al.

(10) Patent No.: US 8,778,838 B2
(45) Date of Patent: *Jul. 15, 2014

(54) AQUEOUS CONCENTRATE FORMULATIONS CONTAINING SAFLUFENACIL AND GLYPHOSATE

(75) Inventors: Michael Krapp, Altrip (DE); Wolfgang Gregori, Ludwigshafen (DE); Sven Adam, Steinweiler (DE); Klaus Kolb, Schifferstadt (DE); Juergen Jakob, Roedersheim-Gronau (DE); Bernd Sievernich, Hassloch (DE); Joerg Steuerwald, Boehl-Iggelheim (DE); Steven Bowe, Apex, NC (US); Joseph Zawierucha, Cary, NC (US); Rex Liebl, Raleigh, NC (US)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/391,898

(22) PCT Filed: Aug. 26, 2010

(86) PCT No.: PCT/EP2010/062471
§ 371 (c)(1),
(2), (4) Date: Feb. 23, 2012

(87) PCT Pub. No.: WO2011/023758
PCT Pub. Date: Mar. 3, 2011

(65) Prior Publication Data
US 2012/0157312 A1    Jun. 21, 2012

Related U.S. Application Data

(60) Provisional application No. 61/237,404, filed on Aug. 27, 2009.

(51) Int. Cl.
| A01N 25/02 | (2006.01) |
| A01N 41/06 | (2006.01) |
| A01N 43/54 | (2006.01) |
| A01N 57/02 | (2006.01) |
| C07C 229/30 | (2006.01) |
| C07C 311/30 | (2006.01) |
| C07D 239/69 | (2006.01) |

(52) U.S. Cl.
USPC ............. 504/127; 504/128; 504/136; 514/75; 514/76; 514/114; 514/269; 514/274; 514/600; 514/603; 514/613; 514/617; 514/642; 544/312; 560/155; 560/231; 562/512; 564/79; 564/86; 564/88; 564/101; 564/123; 564/163; 564/168

(58) Field of Classification Search
USPC ............. 504/127, 128, 136; 514/75, 76, 114, 514/269, 274, 600, 603, 613, 617, 642; 544/312; 560/155, 231; 562/512; 564/79, 86, 88, 101, 123, 163, 168
See application file for complete search history.

(56) References Cited

U.S. PATENT DOCUMENTS

| 4,203,877 | A | 5/1980 | Baker | |
| 6,479,432 | B1 | 11/2002 | Sixl | |
| 8,362,026 | B2 * | 1/2013 | Schmidt et al. | 514/274 |
| 2005/0159622 | A1 | 7/2005 | Hamprecht et al. | |
| 2006/0293520 | A1 | 12/2006 | Hamprecht et al. | |
| 2008/0293941 | A1 | 11/2008 | Gebhardt et al. | |
| 2008/0318781 | A1 * | 12/2008 | Zagar et al. | 504/136 |
| 2010/0105562 | A1 | 4/2010 | Schmidt et al. | |
| 2012/0149577 | A1 * | 6/2012 | Krapp et al. | 504/243 |
| 2012/0157312 | A1 | 6/2012 | Krapp et al. | |
| 2012/0231954 | A1 * | 9/2012 | Krapp et al. | 504/128 |

FOREIGN PATENT DOCUMENTS

| EP | 0000424 | 1/1979 |
| WO | WO 01/22814 | 4/2001 |
| WO | WO 01/30156 | 5/2001 |
| WO | WO 01/83459 | 11/2001 |
| WO | WO 03/024221 | 3/2003 |
| WO | WO 03/097589 | 11/2003 |
| WO | WO 2005/054208 | 6/2005 |
| WO | WO 2006/125746 | 11/2006 |
| WO | WO 2007/014758 | 2/2007 |
| WO | WO 2007/014759 | 2/2007 |
| WO | WO 2008/043835 | 4/2008 |
| WO | WO 2011/023759 | 3/2011 |
| WO | WO 2011/070051 | 6/2011 |
| WO | WO 2011/070054 | 6/2011 |

OTHER PUBLICATIONS

English language translation of the International Preliminary Report on Patentability from corresponding International Application No. PCT/EP2010/062471, filed Aug. 26, 2010.
International Search Report in International Application No. PCT/EP2010/062471, filed Aug. 26, 2010.
Anonymous, "Kixor Herbicide Technical Brochure", BASF Agricultural Products, NC 27709, Jan. 2009, pp. 1-15 (XP000002651574).
Office Action dated Apr. 19, 2013 in U.S. Appl. No. 13/391,896, filed Feb. 23, 2012.

* cited by examiner

*Primary Examiner* — Jane C Oswecki
(74) *Attorney, Agent, or Firm* — Brinks Gilson & Lione

(57) ABSTRACT

The present invention relates to aqueous concentrate formulations for plant protection comprising:
2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in the form of its anhydrate;
N-(phosphonomethyl)glycine in the form of its free acid, in the form of the ammonium salt or a substituted ammonium salt or a mixture thereof;
at least two different non-ionic surfactants with at least one of them comprising an ethylene oxide polymer moiety or an ethylene oxide/$C_3$-$C_4$-alkylene oxide block copolymer moiety, and
water;
wherein the pH-value of the formulation is below 6.

21 Claims, No Drawings

AQUEOUS CONCENTRATE FORMULATIONS CONTAINING SAFLUFENACIL AND GLYPHOSATE

This application is a National Stage application of International Application No. PCT/EP2010/062471 filed Aug. 26, 2010, which claims the benefit of U.S. Provisional Application No. 61/237,404, filed Aug. 27, 2009, the entire contents of which are hereby incorporated herein by reference.

The present invention relates to new aqueous concentrate formulations containing the herbicides saflufenacil and glyphosate. The invention also relates to the use of the formulations for controlling undesired vegetation and to corresponding methods.

For the purpose of application by the end user, herbicide compounds may be formulated in solid forms, such as wettable powders and granules, as well as in liquid forms, such as emulsifiable concentrates (ECs) or suspension concentrates (SCs). The latter ones can be diluted with water for use in the field and thus usually provide an easy-to-handle way of application. However, like many active ingredients that are used as herbicides, saflufenacil is only sparingly soluble in water and mixtures of water with water-miscible solvents such as $C_1$-$C_4$-alkanols or $C_2$-$C_4$-alkandiols and -triols. Nonetheless, application of herbicides in the form of dilute aqueous suspension concentrates, i.e. in the form of spray liquors, is favorable for ease of application.

Suspension concentrates (SC's) are formulations, wherein the active ingredient is present in the form of finely divided solid particles, which are suspended (dispersed) in a liquid dispersing medium such as water or polyhydric alcohols, wherein the active ingredient is usually insoluble or only sparingly soluble (less than 2000 ppm). Suspension concentrates usually contain surface-active compounds (surfactants), such as dispersants and wetting agents for stabilizing the active ingredient particles in the dispersing medium.

Despite the aforementioned advantages associated with the usage of SCs, there are a number of problems known to the skilled person which are sometimes encountered with SCs as a result of settling during prolonged storage or storage at elevated temperatures, the resistance of settled particles to re-suspension and the formation of crystalline material upon storage. As a consequence, the formulations may be difficult to handle and the bioefficacy may be inconsistent.

Saflufenacil is the common name of 2-chloro-5-[3,6-dihydro-3-methyl-2,6-dioxo-4-(trifluoromethyl)-1-(2H)pyrimidinyl]-4-fluoro-N-[[methyl(1-methylethyl)amino]-sulfonyl]benzamide which is a herbicidal compound having the following formula I:

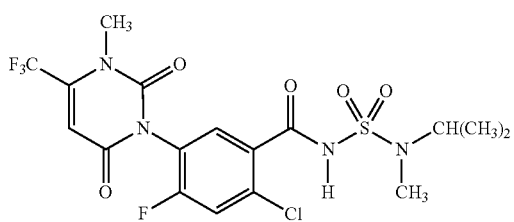

Saflufenacil is a herbicidal active substance which has been disclosed in WO 01/083459. Further processes for its preparation are described in WO 03/097589, WO 05/054208, and WO 06/125746. A crystalline and essentially solvent-free form of saflufenacil, herein after also referred to as the crystalline anhydrate form, is disclosed in WO 08/043835.

Glyphosate is the common name of N-(phosphonomethyl) glycine in the form of its free acid having the following formula II:

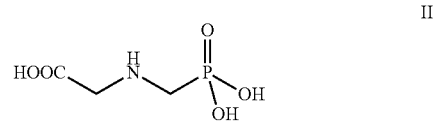

Glyphosate and its salts are non-selective systemic herbicides having a good post-emergence activity against numerous grass weeds. For further reference see for example The Compendium of Pesticide Common Names (http://www.alanwood.net/pesticides/) and C. Tomlin (ed.) "The Pesticide Manual, 14th ed." British Crop Protection Council, Alton Hampshire GB, 2003.

When trying to formulate saflufenacil one faces several problems. Saflufenacil carries a N-amino-sulfonylcarboxamide side-chain which might undergo hydrolysis at elevated temperatures and pH values above 7. Apart from that, saflufenacil is capable of existing in different crystalline and non-crystalline modifications, namely amorphous forms, crystalline hydrates and a crystalline anhydrate, which may undergo uncontrolled interconversion. This interconversion in turn may lead to coarsening of the saflufenacil particles, in particular when formulated as suspension concentrate. These factors might result in a reduced chemical and physical stability of the formulations, an effect that is particularly pronounced when the formulations are stored over prolonged periods of time and/or at elevated temperatures. Said factors may also lead to poor dilution properties as the coarse saflufenacil particles are prone to separate from the diluted formulation.

When trying to formulate saflufenacil together with glyphosate, the situation is further complicated by the fact that glyphosate is typically formulated as an aqueous solution of one of its salts. In particular when high concentrations of glyphosate salt in such formulations are intended the pH of the aqueous formulation is preferably raised above 7, as the glyphosate salts have an increased solubility in that pH range. However, such basic conditions are unfavourable for formulating saflufenacil, due to its aforementioned hydrolytic lability. Moreover high concentrations of glyphosate in surfactant containing aqueous formulations may lead to a demixing of the aqueous phase into water and the surfactants which results in a decreased physical stability of the formulation. High concentrations of glyphosate may also lead to undesired thickening (gelling) of the formulation.

WO 03/024221 discloses combined applications of saflufenacil with a multitude of other herbicides, including glyphosate. Also disclosed are different formulation types that are suitable for formulating the individual actives, including aqueous formulations. However, WO 03/024221 does not describe aqueous concentrate formulations containing both saflufenacil and a further herbicide, and, in particular, WO 03/024221 does not describe aqueous formulations containing both saflufenacil and glyphosate that are stable over extended storage periods.

Up to now, saflufenacil is available only in the form of wettable granule formulations and as emulsion concentrates with low active ingredient loading. An aqueous concentrate formulation of saflufenacil, alone or in combination with a second herbicide, having prolonged storage stability even at elevated temperatures and with good dilution properties has not yet been reported.

Therefore, it is an object of the present invention to provide an aqueous concentrate formulation containing saflufenacil and glyphosate in acid or salt form that shows both high physical and chemical stability over prolonged storage periods while maintaining its biological efficacy. Upon dilution with water, the formulation should give a stable aqueous composition of saflufenacil and glyphosate without forming coarse material or a supernatant liquid.

Surprisingly this object is achieved by formulating saflufenacil in the form of its crystalline anhydrate and glyphosate in the form of the free acid or a salt thereof together with two non-ionic surfactants, one of which having an ethylene oxide polymer moiety or ethylene oxide/alkylene oxide block copolymer moiety, as an aqueous concentrate formulation having a pH value below 6.

Therefore, the present invention relates to an aqueous concentrate formulation for plant protection, comprising the components:
a) 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide(saflufenacil) in the form of its anhydrate;
b) N-(phosphonomethyl)glycine(glyphosate) in the form of its free acid, in the form of the ammonium salt or a substituted ammonium salt, or a mixture thereof;
c) at least two different non-ionic surfactants with at least one of them comprising an ethylene oxide polymer moiety or an ethylene oxide/$C_3$-$C_4$-alkylene oxide block copolymer moiety, and
d) water;
wherein the pH value of the formulation is below 6, e.g. in the range from 1 to below 6, in particular in the range from 1.5 to 5.5 and especially in the range from 2 to 5.

A pH value within the stated range in coaction with the specific non-ionic surfactants unexpectedly imparts a good to excellent overall stability to the formulation of the invention. That is, over prolonged storage periods, the highly active but degradation-prone saflufenacil remains intact in the form of its anhydrate modification and the formulation remains homogenous while affording stable dispersions on dilution. Without being bound to theory it is believed that a pH in the given range stabilizes the anhydrate form while the specific mix of surfactant provides for a stable suspension of the saflufenacil particles and a homogeneous distribution of glyphosate or its salt in the formulation. Thus, by employing the mentioned non-ionic surfactants and adjusting the pH value within the given range it is surprisingly possible to balance the chemical stability of the anhydrate form with the physical stability of the formulation. Moreover the surfactants and the pH value required for the formulations of the invention are essential for avoiding undesirable thickening, in particular at high glyphosate concentrations.

In conclusion, the aqueous concentrate formulations of the present invention exhibit good physical and chemical stability over prolonged storage times. Thus neither significant phase separation phenomena such as agglomeration of the active ingredients or demixing of the aqueous phase occur nor does the saflufenacil anhydrate degrade to a noticeable extent or change into a different modification.

As used herein, $C_3$-$C_4$-alkylene oxide refers to an epoxide ring wherein the carbon atoms of the epoxide ring is substituted with one or two methyl groups or with one ethyl group. Specifically, $C_3$-$C_4$-alkylene oxide refers to propylene oxide, 1,2-butylene oxide, cis- or trans-2,3-butylene oxide and/or isobutylene oxide.

As used herein, $C_2$-$C_5$ alkanediol refers to a cyclic, straight-chained or branched alkanols which have from 2 to 5 carbon atoms and which carry two OH moieties, examples including ethylene glycol, 1,2-propanediol, 1,3-propanediol, 1,4 butanediol and 2,4-pentanol.

As used herein, $C_3$-$C_8$ alkanediol refers to a cyclic, straight-chained or branched alkanols which have from 3 to 8 carbon atoms and which carry three OH moieties, examples including glycerol, 1,2,3-butanetriol, 1,2,4-butanetriol, 1,3,5-cyclohexanetriol, 2,4,6-heptanetriol and 3-methyl-pentane-1,2,4-triol.

As used herein, substituted ammonium refers to an ammonium counter ion of a salt, wherein 1, 2, 3, or 4 hydrogen atoms of the ammonium ion are replaced with $C_1$-$C_6$-alkyl radicals which are unsubstituted or substituted with halogen, CN, OH, optionally substituted $C_1$-$C_6$-alkoxy and/or optionally substituted aryl. Examples for substituted ammonium are methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di-(2-hydroxyeth-1-yl)ammonium, benzyltrimethylammonium, benzyltriethylammonium.

As used herein "concentrate formulation" refers to a pesticidal formulation that contains at least 10% by weight, preferably at least 15% by weight and in particular at least 20% by weight, e.g. from 10 to 60% by weight, in particular from 15 to 55% by weight or from 20 to 50% by weight, based on the total weight of the formulation, of active ingredients, i.e. in the formulations according to the invention saflufenacil plus glyphosate or a salt thereof.

As stated before, the crystalline anhydrate form of saflufenacil employed in the formulation of the invention refers to the saflufenacil modification that has been disclosed in WO 08/043835. Accordingly, the crystalline anhydrate form is an essentially solvent-free crystalline form of saflufenacil (compound of formula I). In this connection the term "essentially solvent-free" means that the crystalline anhydrate form comprises no detectable amounts of solvents incorporated into the crystal lattice, i.e. the amount of solvent in the crystal lattice is less than 10 mol %, in particular not more than 5 mol %, based on saflufenacil.

The crystalline anhydrate form can be identified by means of X-ray powder diffractometry on the basis of its diffraction diagram. Thus, an X-ray powder diffractogram recorded at 25° C. using Cu—Kα radiation (1.54178 Å) shows at least 2, as a rule at least 4, frequently at least 6, in particular at least 8 and specifically all of the reflexes detailed in Table 1 hereinbelow as 2θ values, or as interplanar spacings d:

TABLE 1

| 2θ | d [Å] |
|---|---|
| 6.3 ± 0.2° | 14.92 ± 0.3 |
| 9.4 ± 0.2° | 9.37 ± 0.2 |
| 10.9 ± 0.2° | 8.15 ± 0.1 |
| 11.9 ± 0.2° | 7.45 ± 0.05 |
| 12.6 ± 0.2° | 7.02 ± 0.05 |
| 15.0 ± 0.2° | 5.90 ± 0.05 |
| 15.8 ± 0.2° | 5.62 ± 0.04 |
| 17.1 ± 0.2° | 5.19 ± 0.03 |
| 20.0 ± 0.2° | 4.44 ± 0.02 |

TABLE 1-continued

| 2θ | d [Å] |
|---|---|
| 20.4 ± 0.2° | 4.36 ± 0.02 |
| 24.7 ± 0.2° | 3.61 ± 0.02 |
| 25.2 ± 0.2° | 3.53 ± 0.02 |
| 26.2 ± 0.2° | 3.40 ± 0.02 |

Studies on monocrystals of the anhydrate form at −170° C. demonstrate that the underlying crystal structure is monoclinic. The unit cell has the space group P2(1)/c. The characteristic data of the crystal structure of the anhydrate form are compiled in Table 2.

TABLE 2

Crystallographic characteristics of the crystalline anhydrate form (measured at −170° C.)

| Parameter | Form II |
|---|---|
| class | monoclinic |
| space group | P2(1)/c |
| a | 9.377(5) Å |
| b | 7.698(4) Å |
| c | 28.12(2) Å |
| α | 90° |
| β | 96.37(3)° |
| γ | 90° |
| volume | 2017.1(17) Å 3 |
| Z | 4 |
| density (calculated) | 1.649 mg/m$^3$ |
| R1; wR2 | 0.057; 0.149 |
| wavelength | 1.54178 Å | a, b, c = unit cell length
α, β, γ = unit cell angle
Z = number of molecules in the unit cell Besides X-ray powder diffractometry and the crystallographic analysis, differential scanning calorimetry (DSC) can also be employed for identifying the anhydrate form. Thus, the anhydrate form shows a thermogram with a characteristic melting peak in the range between 170 and 200° C. The peak maximum is typically in the range of approximately 180° C. to 190° C. The melting points indicated herein refer to data determined by means of DSC, crucible material aluminum, heating rate 5 K/min).

The crystalline anhydrate form of saflufenacil may be prepared by controlled crystallization from a solution of saflufenacil in an organic solvent which is essentially free from water as described in WO 08/043835.

Generally, the concentrate formulations of the present invention comprise the crystalline anhydrate modification of saflufenacil, herein also referred to as saflufenacil anhydrate, in a finely divided particulate form, where the particles of the saflufenacil anhydrate are suspended in an aqueous phase. Likewise, glyphosate, in particularly if present in its free acid form, may also be included in the formulation in the form of finely divided solid particles. However, glyphosate may also be present in dissolved form. The size of the active substance particles, i.e. the diameter of the active substance particles, will in general not exceed 20 μm, preferably not exceed 10 μm and in particular not exceed 5 μm. The particle size given is the so called $D_{90}$-value, which has to be understood as the value that is not exceeded by the diameters of at least 90% by weight of the particles. The active substance particles have an average particle diameter, herein also termed $D_{50}$-value, ranging preferably from 0.5 to 20 μm, in particular from 1 to 5 μm. The $D_{50}$-value is defined as the value that is above the diameters of 50% by weight of the particles and below the diameters of 50% by weight of the particles. Advantageously, at least 40% by weight, preferably at least 60% by weight and in particular at least 80% by weight of the particles in the aqueous concentrate formulations according to the invention have sizes, i.e. diameters, of below 3 μm. The particle size of the active substance particles (i.e. the diameters) can be determined by conventional methods such as light-scattering.

The particles of saflufenacil anhydrate contained in the formulation of the invention are solid a.i. particles, i.e. the particles mainly contain the pure saflufenacil anhydrate. The purity of the saflufenacil anhydrate is usually at least 90% by weight, preferably at least 95% and in particular at least 97% by weight.

The concentration of saflufenacil anhydrate in the formulation of the invention may usually be from 0.01 to 20% by weight, in particular from 0.1 to 15% by weight, more preferably from 1 to 10% by weight or 1 to 5% by weight, based on the total weight of the formulaton.

The glyphosate material contained in the formulation is present in homogeneously distributed form, i.e. there is no visible macroscopic formation of distinct phases or other visible separation of material. Glyphosate as the free acid and/or a salt thereof may be present in the formulation of the invention in a dissolved form or in the form of finely divided particles. Alternatively it may be present in the formulation of the invention as a mixture of both dissolved form and particulate form. In any case the particulate form and the dissolved form are homogenously distributed within the formulation.

The concentration of glyphosate as the free acid and/or its salt in the formulation of the invention may usually be from 10 to 55% by weight, in particular from 15 to 50% by weight, more preferably from 20 to 45% by weight, based on the total weight of the formulaton.

In the aqueous concentrate formulations of the invention the weight ratio of saflufenacil (component a)) to glyphosate in acid or salt form (component b)) is usually in the range from 1:1 to 1:1000, preferably in the range from 1:2 to 1:500, more preferably in the range from 1:4 to 1:250, even more preferably in the range from 1:5 to 1:150, particularly in the range from 1:6 to 1:50 and specifically in the range from 1:7 to 1:20. Particularly preferred is a weight ratio of components a) to b) of about 1:12.

According to the invention, the saflufenacil anhydrate is insoluble or only sparingly soluble in the aqueous phase of the formulations at the above pH values, i.e. at 25° C./1013 mbar the solubility of the saflufenacil anhydrate in the aqueous phase of the formulation is not more than 1% by weight, in particular not more than 0.1% by weight and specifically not more than 0.01% by weight.

In the context of this invention the term "aqueous phase" stands for the liquid component of the formulation comprising an aqueous solvent and compounds solved therein. The aqueous solvent of the present invention is either water or a mixture thereof with a water-miscible organic solvent, which is selected from $C_2$-$C_5$-alkanediols and $C_3$-$C_8$-alkanetriols, preferably from the group consisting of ethylene glycol, 1,2-propanediol, 1,3-propanediol, glycerol and 1,4-butanediol, and more preferably from 1,2-propanediol and 1,3-propanediol. According to a particular preferred embodiment of the invention the organic solvent is 1,2-propanediol.

The amount of aqueous solvent in the formulation of the invention may usually be from 10 to 88,9% by weight or from 10 to 85% by weight, in particular from 15 to 81% by weight or from 15 to 80% by weight or 10 to 79,8% by weight and more preferably from 15 to 76% by weight or from 20 to 76% by weight or from 30 to 76% by weight, based on the total weight of the formulation.

In a first preferred embodiment of the invention the aqueous solvent consists mainly of water, i.e. water makes up at least 99% by weight of the total amount of solvent present in the formulation. In a more preferred embodiment of the invention the aqueous solvent is a mixture of the aforementioned water-miscible organic solvent and water. In the latter case, the weight ratio of water to water-miscible organic solvent in the aqueous solvent preferably is in the range of from 99.9:0.1 to 1:1.5; more preferably in the range of from 99.5:0.5 to 3:1; and most preferably in the range of from 99:1 to 5:1. Expressed differently the amount of organic solvent may preferably be from 0.1 to 20% by weight, more preferably from 0.1 to 15% by weight, and most preferably from 0.1 to 10% by weight, based on the total weight of the formulation.

According to a preferred embodiment of the invention the component c) comprises at least one ethylene oxide/$C_3$-$C_4$-alkylene oxide block copolymer which is hereinafter referred to as surfactant c1). The surfactant c1) is selected form non-ionic block copolymers comprising at least one poly(ethylene oxide) moiety PEO and at least one polyether moiety PAO derived from $C_3$-$C_4$-alkylene oxides, in particular selected from ethylene oxide/propylene oxide block copolymers.

The at least one PAO moiety of a non-ionic block copolymer c1) usually comprises at least 3, preferably at least 5, in particular 10 to 100 repeating units (number average) which are derived from $C_3$-$C_4$ alkylene oxides, such as propylene oxide, 1,2-butylene oxide, cis- or trans-2,3-butylene oxide or isobutylene oxide. Preferably, the PAO moieties comprise at least 50% by weight, and more preferably at least 80% by weight of repeating units derived from propylene oxide. The at least one PEO moiety of a non-ionic block copolymer c1) usually comprise at least 3, preferably at least 5, and more preferably at least 10 repeating units derived from ethylene oxide (number average). The weight ratio of PEO moieties and PAO moieties (PEO:PAO) usually ranges from 1:10 to 10:1, preferably from 1:10 to 2:1, more preferably from 2:8 to 7:3 and in particular from 3:7 to 6:4. Those surfactants c1) are preferred which have a number average molecular weight $M_N$ ranging from more than 1200 to 100000 Dalton, preferably from 2000 to 60000 Dalton, more preferably from 2500 to 50000 Dalton and in particular from 3000 to 20000 Dalton. In general, the PEO moieties and the PAO moieties make up at least 80% by weight, and preferably at least 90% by weight, e.g. 90 to 99.5% by weight, of the non-ionic block copolymer surfactants c1). Suitable surfactants c1) are described e.g. in WO 06/002984, in particular those having the formulae P1 to P5 given therein.

The non-ionic block copolymer surfactants c1) described herein are commercially available e.g. under the trade names Pluronic®, such as Pluronic® PE 3100, PE 3500, PE 4300, PE 6100, PE 61200, PE 6200, PE 6400, PE 6800, PE 8100, PE 9200, PE 9400, PE 10100, PE 10400, PE 10500, RPE 1720, RPE 1740, RPE 2520, RPE 2525 and RPE 3110 (BASF SE). Among these particularly suitable examples are Pluronic® PE 6400, Pluronic® PE 10500 and the like.

The total amount of surfactants c1), if present, is preferably in the range from 0.5 to 35% by weight, in particular from 1 to 30% by weight, more preferably from 1 to 25% by weight, based on the total weight of the formulation.

According to an embodiment of the present invention the component c) comprises at least one surfactant that in addition to an ethylene oxide polymer moiety or an ethylene oxide/$C_3$-$C_4$-alkylene oxide block copolymer moiety comprises a further, different moiety. Such surfactants are preferably selected from the surfactant groups c2), c3) and c4) as defined herein below.

The non-ionic surfactants of group c2) are selected from polyethoxylates and poly-ethoxylates-co-propoxylates of linear or branched $C_3$-$C_{20}$-alkanoles, such as polyethoxylated or poly-ethoxy-co-propoxylated $C_8$-$C_{20}$-fatty alcohols and poly-ethoxy-co-propoxylated $C_3$-$C_{20}$-oxoalcohols. Examples of non-ionic surfactants c2) are polyethoxylated lauryl alcohol, polyethoxylated isotridecanol, polyethoxylated cetyl alcohol, poly-ethoxylates-co-propoxylates of octanol, poly-ethoxylates-co-propoxylates of 2-ethyl-hexanol, poly-ethoxylates-co-propoxylates of heptanol, poly-ethoxylates-co-propoxylates of hexanol, poly-ethoxylates-co-propoxylates of 2-ethyl-propanol, poly-ethoxylates-co-propoxylates of butanol, poly-ethoxylates-co-propoxylates of iso-butanol, poly-ethoxylates-co-propoxylates of tert-butanol and poly-ethoxylates-co-propoxylates of propanol. Preferred non-ionic surfactants c2) are poly-ethoxy-co-propoxylated $C_3$-$C_{10}$-alkanols and particularly preferred is poly-ethoxy-co-propoxylated butanol. The non-ionic surfactants of the group c2) described herein are commercially available e.g. under the trade name Atlas G 5000 (Croda).

The non-ionic surfactants of group c3) are selected from polyethoxylates of polyol esters, wherein the polyols may be partially or completely esterified with saturated or unsaturated $C_6$-$C_{22}$-alkanoic acids, such as mono-, di- and triesters of glycerine and mono-, di-, tri-, tetra-, penta- and hexaesters of sorbitol. Examples of non-ionic surfactants of group c3) are polyethoxylates of glycerine monostearate, polyethoxylates of sorbitol monooleat and polyethoxylates of sorbitol hexaoleat. Preferred non-ionic surfactants c3) are polyethoxylates of esters of sorbitol with $C_6$-$C_{22}$-alkanoic acids, in particular preferred are polyethoxylates of sorbitol hexaoleate. The non-ionic surfactants of the group c3) described herein are commercially available e.g. under the trade name Atlas G 1086 (Croda).

The terms polyethoxylate and polyethoxylated refer to polyether radicals derived from ethyleneoxide. Likewise, the terms poly-ethoxy-co-propoxylate and poly-ethoxy-co-propoxylated refers to a polyether radical derived from a mixture of ethyleneoxide and propylenoxide. Thus polyethoxylates have repeating units of the formula [$CH_2CH_2O$] while poly-ethoxy-co-propoxylate have repeating units of the formulae [$CH_2CH_2O$] and [$CH(CH_3)CH_2O$]. In the surfactants of these groups, the number of such repeating units will generally range from 2 to 200, in particular from 3 to 100, especially from 3 to 50.

The non-ionic surfactants of group c4) are selected from reaction products of polyethylenimine with an optionally hydroxylated saturated or unsaturated $C_{12}$-$C_{24}$-fatty acid. Of said reaction products those are preferred that mainly consist of comb-shaped compounds resulting from the amidation of polyethylenimines with hydroxylated saturated $C_{12}$-$C_{24}$-fatty acids and in particular with 12-hydroxyl-octadecanoic acid. The non-ionic surfactants of the group c4) described herein are commercially available e.g. under the trade name Tersperse® 4890 (Huntsman).

According to preferred embodiment of the invention in addition to at least one surfactant c1), the component c) further comprises at least one non-ionic surfactant selected from the groups c2), c3) and c4).

According to a particular preferred embodiment of the invention the component c) comprises at least one surfactant c1), which is preferably selected from ethylene oxide/propylene oxide block copolymers, and at least one non-ionic surfactant of group c3), which is preferably selected from polyethoxylates of esters of sorbitol with $C_6$-$C_{22}$-alkanoic acids and more preferably selected from polyethoxylates of sorbitol hexaoleate.

According to another particular preferred embodiment of the invention the component c) comprises at least one surfactant c1), which is preferably selected from ethylene oxide/propylene oxide block copolymers and at least one surfactant of group c4), which is preferably selected from reaction products of polyethylenimines with an optionally hydroxylated saturated or unsaturated $C_{12}$-$C_{24}$-fatty acid and more preferably selected from reaction products of polyethylenimines with 12-hydroxyl-octadecanoic acid.

According to another particular preferred embodiment of the invention the component c) comprises at least one surfactant of group c1) and at least one surfactant of group c4), both as described herein before, and in addition at least one surfactant of group c3), which is preferably selected from polyethoxylates of esters of sorbitol with $C_6$-$C_{22}$-alkanoic acids and more preferably selected from polyethoxylates of sorbitol hexaoleate.

According to further embodiments of the invention the component c) comprises a combination of at least one surfactant c2) and at least one surfactant c3), or of at least one surfactant c2) and at least one surfactant c4), or of at least one surfactant c3) and at least one surfactant c4). In these combinations the surfactants c2), c3) and c4) are as described herein before.

According to preferred embodiment of the invention the component c) comprises at least one surfactant c2), at least one surfactant c3) and at least one surfactant c4), all of which as described before. In this context preference is given to poly-ethoxy-co-propoxylated $C_3$-$C_{20}$-alkanols as surfactants c2), polyethoxylates of the esterification product of sorbitol with oleic acid as surfactants c3) and reaction products of polyethylenimine with a hydroxylated saturated $C_{12}$-$C_{24}$-fatty acid as surfactants c4).

According to another particular preferred embodiment of the invention in addition to the component c), in particular in addition to any of the herein before described combinations of at least one non-ionic surfactant c1) with at least one further non-ionic surfactant selected from groups c2) to c4), the formulations of the invention also comprise, as a component e), an anionic surfactant, which is preferably selected from the compounds of the groups e1), e2) and e3), as defined herein below.

The anionic surfactants of group e1) are selected from $C_1$-$C_{16}$-alkylarene sulfonates, such as mono-, di- and tri-$C_1$-$C_{16}$-alkylbenzene sulfonates and mono-, di- and tri-$C_1$-$C_{16}$-alkylnaphthaline sulfonates and their salts, in particular their alkaline metal salts, such as the sodium or potassium salts, or their earth alkaline metal salts, in particular the calcium salts, or their ammonium salts. Examples of anionic surfactants of group e1) are dibutylnaphtaline sulfonate, dodecyldiphenylether sulfonate, cumyl sulfonate, octylbenzene sulfonate, nonylbenzene sulfonate, dodecylbenzene sulfonate and tridecylbenzene sulfonate and their salts. Preferred surfactants e1) are mono- or di-$C_4$-$C_8$-alkylnaphthaline sulfonic acids and mono- or di-$C_4$-$C_{16}$-alkylbenzesulfonic acids and their salts in particular their alkaline metal salts, such as the sodium or potassium salts, or their earth alkaline metal salts, in particular the calcium salts, or their ammonium salts.

The anionic surfactants of group e2) are selected from sulfated polyethoxylates of di- or tristyryl phenol and from their salts, in particular their alkaline metal salts, such as the sodium or potassium salts, or their earth alkaline metal salts, in particular the calcium salts, or their ammonium salts.

The anionic surfactants of group e3) are selected from polymeric anionic surfactants having $SO_3^-$ groups bound to an aromatic moiety such as a phenyl or a naphthyl ring, e.g. condensates of arylsulfonic acid with formaldehyde and optionally in addition with urea, such as naphthalene sulfonic acid formaldehyde condensates, phenol sulfonic acid formaldehyde condensates, cresol sulfonic acid formaldehyde condensates, ligninsulfonates, etc and from their salts, in particular their alkaline metal salts, such as the sodium or potassium salts, or their earth alkaline metal salts, in particular the calcium salts, or their ammonium salts. The arylsulfonic acids incorporated into said formaldehyde condensates may be e.g. phenol sulfonic acids or naphthalene sulfonic acids which are unsubstituted or substituted by one or more, e.g. 1, 2, 3 or 4 $C_1$-$C_{20}$ alkyl groups. In a preferred embodiment, the surfactant e3) is an alkaline metal salt or earth alkaline metal salt of a reaction product (condensate) of phenol sulfonic acid and formaldehyde; particularly suitable examples are Tamol® DN (BASF), Tamol® PP (BASF) and Wettol® D1 (BASF).

Preferred anionic surfactants e) are those of group e3), in particular condensation products of phenol sulfonic acid and formaldehyde and their salts, in particular their alkaline metal salts, such as the sodium or potassium salts, or their earth alkaline metal salts, in particular the calcium salts, or their ammonium salts.

The total amount of anionic surfactant e), if present, is preferably in the range from 0.01 to 15% by weight, in particular from 0.05 to 10% by weight, more preferably from 0.1 to 5% by weight, based on the total weight of the formulation.

According to yet another preferred embodiment of the present invention the formulation of the invention comprises:
  from 0.1 to 15, frequently from 1 to 10% by weight, preferably from 1 to 5% by weight, based on the total weight of the composition, of saflufenacil in the form of its crystalline anhydrate;
  from 10 to 55% by weight, frequently from 15 to 50% by weight, preferably from 20 to 45% by weight, in particular from 25 to 40% by weight, based on the total weight of the composition, of glyphosate in the form of its free acid, in the form of its ammonium salt or its substituted ammonium salt, or a mixture thereof;
  from 1 to 30% by weight, frequently from 3 to 30% by weight, preferably from 5 to 25% by weight, based on the total weight of the composition, of at least two different non-ionic surfactants with at least one of them comprising an ethylene oxide polymer moiety or an ethylene oxide/$C_3$-$C_4$-alkylene oxide block copolymer moiety; and
  from 10 to 88,9% by weight, frequently from 15 to 81% by weight or from 15 to 76% by weight or from 30 to 76% by weight, based on the total weight of the composition, of an aqueous solvent.

The compositions according to the invention may also comprise customary adjuvants, such as viscosity-modifying additives (thickeners), antifoam agents, preservatives, buffers, inorganic dispersants, etc, which are usually employed in aqueous formulations of herbicides. Such adjuvants may be incorporated into the formulations of the invention either before or after step (ii) of the preparation process described herein has been carried out. Preferably the adjuvants are added after completion of step (ii) and before step (iv) of the preparation process. The amount of additives will generally not exceed 15% by weight, in particular 10% by weight of the total weight of the composition.

Suitable inorganic dispersants, also termed anticaking agents, for preventing agglutination of the a.i. particles, are silica (such as, for example Sipernat® 22 from Degussa), alumina, calcium carbonate and the like. In the context of the present invention silica is a preferred inorganic dispersant. The concentration of inorganic dispersants in the final aqueous concentrates will generally not exceed 3% by weight, based on the total weight of the final aqueous concentrate, and is preferably in the range from 0.01 to 3% by weight, in particular from 0.02 to 1.5% by weight and especially from 0.1 to 1% by weight, based on the total weight of the final suspension concentrate.

Suitable thickeners are compounds which affect the flow behavior of the suspension concentrate and may assist in stabilizing the suspension concentrate against caking. Mention may be made, in this connection, for example, of commercial thickeners based on polysaccharides, such as methylcellulose, carboxymethylcellulose, hydroxypropylcellulose (Klucel® grades), Xanthan Gum (commercially available e.g. as Kelzan® grades from Kelco or Rhodopol® grades from Rhodia), synthetic polymers such as acrylic acid polymers (Carbopol® grades), polyvinyl alcohol (e.g. Mowiol® and Poval® grades from Kuraray) or polyvinyl pyrrolones, silicic acid or phyllosilicates such as montmorillonite and bentonites, which may be hydrophobized, (commercially available as Attaclay® grades and Attaflow® grades from BASF SE; or as Veegum® grades and Van Gel® grades from R.T. Vanderbilt). In the context of the present invention Xanthan Gum is a preferred thickener. The concentration of thickeners in the final suspension concentrates will generally not exceed 3% by weight, based on the total weight of the final suspension concentrate, and is preferably in the range from 0.1 to 3% by weight, in particular from 0.5 to 2.5% by weight and especially from 1 to 2.2% by weight, based on the total weight of the final suspension concentrate.

Antifoam agents suitable for the formulations according to the invention are, for example, silicone emulsions (such as, for example, Silicone SRE-PFL from Wacker or Rhodorsil® from Rhodia), long-chain alcohols, fatty acids, organofluorine compounds and mixtures thereof.

Suitable preservatives to prevent microbial spoiling of the compositions of the invention include formaldehyde, alkyl esters of p-hydroxybenzoic acid, sodium benzoate, 2-bromo-2-nitropropane-1,3-diol, o-phenylphenol, thiazolinones, such as benzisothiazolinone, 5-chloro-2-methyl-4-isothiazolinone, pentachlorophenol, 2,4-dichlorobenzyl alcohol and mixtures thereof. Commercially available preservatives that are based on isothiazolinones are for example marketed under the trademarks Proxel® (Arch Cheimical), Acticide® MBS (Thor Chemie) and Kathon® MK (Rohm & Haas).

If appropriate, the aqueous concentrate formulations according to the invention may comprise buffers to regulate the pH. Examples of buffers are alkali metal salts of weak inorganic or organic acids such as, for example, phosphoric acid, boric acid, acetic acid, propionic acid, citric acid, fumaric acid, tartaric acid, oxalic acid and succinic acid.

In addition, the aqueous concentrate formulations according to the invention can be formulated with conventional binders, for example aqueous polymer dispersions, water-soluble resins, for example water-soluble alkyd resins, or waxes.

The formulations of the present invention can be prepared by a process comprising the following steps:
(i) providing a suspension of saflufenacil anhydrate in a mixture of the aqueous solvent, the surfactants c) and e) and optionally the glyphosate compound(s) of component b), wherein the amounts of aqueous solvent, the surfactants and/or component b) intended for the formulation are used in full or in part;
(ii) reducing the size of particles of saflufenacil anhydrate and, if applicable, also of particles of component b) present in the suspension of step (i), preferably to the size specified above;
(iii) if applicable, blending the mixture obtained in step (ii) with the remaining amounts of aqueous solvent, of the surfactants and of component b) and homogenizing the mixture, wherein said remaining amount in each case is the fraction of the respective amount intend for the formulation minus the amount already added in step (i);
(iv) optionally adjusting the pH to a value below 6, if necessary.

In order to prepare the suspension of step (i), the saflufenacil anhydrate, the aqueous solvent, the surfactants and optionally component b) are mixed in any conventional mixing device which is capable of providing sufficient shear to form the desired suspension. Suitable mixing devices include in particular high shear mixers, such as Ultra-Turrax apparatus, static mixers, e.g. systems having mixing nozzles, agitator bead mills, colloid mills, cone mills and other homogenizers.

In general, the sequence in which the individual components are combined is not critical. However, it may be advantageous to carry step (i) out by firstly mixing the solvent, the surfactant and optionally component b), if required at an elevated temperature of 10° C. to 40° C., until a homogenous mixture is obtained, and then adding the saflufenacil anhydrate with shear to said homogenous mixture. Thus, step (i) yields a mixture including the components a), c), d) and optionally b), wherein saflufencacil (component a)) is present in the form of solid particles which are dispersed in the homogeneous phase formed mainly by the solvent and the surfactant.

The mixture obtained from step (i), i.e. in the form of a suspension, is subjected in step (ii) to suitable means for reducing the particle size of the saflufenacil anhydrate particles and, if applicable, particles of component b) present in the mixture typically to below 20 µm, preferably to below 10 µm and in particular to below 5 µm ($D_{90}$-value). The step (ii) may be carried out by any physical attrition method, such as grinding, crushing or milling, in particular by wet grinding or wet milling, including e.g. bead milling, hammer milling, jet milling, air classifying milling, pin milling, cryogenic grinding processes and the like.

Steps (i) and (ii) are usually performed subsequently. However it is also possible to perform these steps together.

According to a preferred embodiment of the present invention the component b) intended for the formulation to be prepared is not included in step (i). Instead, component b) is added in step (iii) to the mixture from step (ii), typically together with a portion of the surfactants and optionally also a portion of the aqueous solvent. The resulting mixture is then homogenized, if required at an elevated temperature of 10° C. to 40° C., using in particular those mixing devices, that are described above as suitable for step (i).

If necessary, i.e. if the pH of the aqueous suspension obtained in steps (ii) or (iii) is outside the range according to the invention, the pH of the suspension obtained in steps (ii) or (iii) will be adjusted in step (iv) to the claimed range. The adjustment of the pH value of the formulation in step (iv) can be effected in manner known per se using methods for pH measurement well known in the art, in particular those employing a pH electrode. The pH is usually adjusted by adding an acid or a base to the aqueous suspension obtained in steps (ii) or (iii). However, a suitable buffer providing a pH in the desired range may also be added. Preferred acids for this purpose are dilute mineral acids such as HCl, $HNO_3$, $H_2SO_4$ or $H_3PO_4$, or dilute organic acids such as acetic acid. Preferred bases in this regard are dilute alkali metal hydroxides such as NaOH or KOH, and alkaline earth metal hydroxides such as magnesium hydroxide or calcium hydroxide. Preferably, the pH is adjusted with dilute acetic acid. By this means the pH is brought to a value of below 6, in particular to a value in the range of from 1.5 to 5.5 and especially in the range of from 2 to 5.

Step (iv) is usually performed subsequent to steps (i), (ii) and (iii) so that its completion affords the final aqueous concentrate formulation according to the present invention. Alternatively, step (iv), if required, may be performed prior to step (ii) or prior to step (iii).

The invention also relates to uses of the aqueous concentrate formulation of the invention for protecting crop plants and to methods of controlling undesired vegetation, which comprise applying the formulations, in diluted or undiluted form, to plants, their environment and/or seeds.

The herbicidal formulations of the invention affect a very good control of vegetation in non-crop areas, especially at high application rates. In crops such as soybean, cotton, oilseed rape, flax, lentils, rice, sugar beet, sunflower, tobacco and cereals, such as, for example maize or wheat, they are active against broad-leaved weeds and grass weeds without inflicting substantial damage to the crop plants. This effect is particularly observed at low application rates.

Depending on the application method in question, the formulations of the invention can additionally be employed in a further number of crop plants to remove undesired plants. Crops which are suitable are, for example, the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica* (*Coffea canephora, Coffea liberica*), *Cucumis sativus, Cynodon dactylon, Daucus carota, Elaeis guineensis, Fragaria vesca, Glycine max, Gossypium hirsutum,* (*Gossypium arboreum, Gossypium herbaceum, Gossypium vitifolium*), *Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum* (*N. rustica*), *Olea europaea, Oryza sativa, Phaseolus lunatus, Phaseolus vulgaris, Picea abies, Pinus* spec., *Pisum sativum, Prunus armeniaca, Prunus avium, Prunus cerasus, Prunus dulcis, Prunus domesticua, Prunus persica, Pyrus communis, Ribes sylvestre, Ricinus communis, Saccharum officinarum, Secale cereale, Solanum tuberosum, Sorghum bicolor* (*s. vulgare*), *Theobroma cacao, Trifolium pratense, Triticum aestivum, Triticum durum, Vicia faba, Vitis vinifera* and *Zea mays*.

In addition, the formulations of the invention can also be used in crops which tolerate the effect of herbicides as the result of breeding, including genetic engineering methods.

Furthermore, the formulations of the invention can also be used in crops which tolerate attack by insects or fungi as the result of breeding, including genetic engineering methods.

Moreover, it has been found that the formulations of the invention are also suitable for the defoliation and desiccation of plant parts, for which crops plants such as cotton, potato, oilseed rape, sunflower, soybean or field beans, in particular cotton, are suitable.

As desiccants, the formulations of the invention are particularly suitable for desiccating the aerial parts of crop plants such as potato, oilseed rape, sunflower and soybean. This makes possible the fully mechanical harvesting of these important crop plants. Also of economic interest is to facilitate harvesting, which is made possible by concentrating within a certain period of time the dehiscence, or reduction of adhesion to the tree, in citrus fruit, olives or other species and varieties of pome fruit, stone fruit and nuts. The same mechanism, i.e. the promotion of the development of abscission tissue between fruit part or leaf part and shoot part of the plants is also essential for the controlled defoliation of useful plants, in particular cotton. Moreover, a shortening of the time interval within which the individual cotton plants mature leads to an increased fiber quality after harvesting.

Moreover, it has been found that the formulations of the invention are also suitable for the control of conifers, in particular of conifer seedlings which grow naturally, and specifically for the control of pine seedlings which grow naturally.

In general, the aqueous concentrate formulations described herein are useful for combating undesired vegetation. For this purpose, the formulations may be applied as such or are preferably applied after dilution with water. Preferably, for various purposes of end user application, a so-called aqueous spray-liquor is prepared by diluting the aqueous concentrate formulation of the present invention with water, e.g. tap water. The spray-liquors may also comprise further constituents in dissolved, emulsified or suspended form, for example fertilizers, active substances of other groups of herbicidal or growth-regulatory active substances, further active substances, for example active substances for controlling animal pests or phytopathogenic fungi or bacteria, furthermore mineral salts which are employed for alleviating nutritional and trace element deficiencies, and nonphytotoxic oils or oil concentrates. As a rule, these constituents are added to the spray mixture before, during or after dilution of the formulations according to the invention.

The formulations of the invention can be applied by the pre-emergence or the post-emergence method. If saflufenacil and/or glyphosate are less well tolerated by certain crop plants, application techniques may be employed where the herbicidal compositions are sprayed, with the aid of the spraying apparatus, in such a way that the leaves of the sensitive crop plants ideally do not come into contact with them, while the active substances reach the leaves of undesired plants which grow underneath, or the bare soil surface (post-directed, lay-by).

Depending on the aim of the control measures, the season, the target plants and the growth stage, the formulations of the invention are applied to such a degree that the application rates of saflufenacil are from 0.001 to 3.0, preferably from 0.01 to 1.0 kg/ha active substance (a.s.).

To widen the spectrum of action and to obtain synergistic effects, the aqueous concentrate formulations of the invention can be mixed with a large number of representatives of other groups of herbicidal or growth-regulatory active substances and applied together with these.

Examples of suitable mixing partners are 1,2,4-thiadiazoles, 1,3,4-thiadiazoles, amides, aminophosphoric acid and its derivatives, aminotriazoles, anilides, aryloxy/heteroaryloxyalkanoic acids and their derivatives, benzoic acid and its derivatives, benzothia-diazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetero-aryloxyphenoxypropionic acid esters, phenylacetic acid and its derivatives, 2-phenyl-propionic acid and its derivatives, pyrazoles, phenylpyrazoles, pyridazines, pyridine-carboxylic acid and its derivatives, pyrimidyl ethers, sulfonamides, sulfonylureas, triazines, triazinones, triazolinones, triazolecarboxamides and uracils.

It is of also possible to use the aqueous suspension concentrate formulations of the present invention as a tank-mix partner with other formulations. Thus, the formulations of the invention can be mixed and applied together with a large number of different pesticide compound formulations, for example those that include active ingredients or adjuvants, such as atrazine, glyphosate, glufosinate, S-metolachlor, 2,4-D ester, isoxaflutole, diflufenzopyr, dicamba, mesotrione, dimethenamid-P, pendimethalin, imazethapyr, paraffin oils, polyol fatty acid esters, polyethoxylated polyol fatty acid esters, ethoxylated alkyl aryl phosphates, methylated seed oils, emulsifiers, ammonium sulfate or mixtures thereof.

Moreover, it may be useful to apply the formulations of the invention, separately or in combination with other herbicides, jointly as a mixture with yet further plant protection agents, for example with agents for controlling pests or phytopathogenic fungi or bacteria. Also of interest is the miscibility with mineral salt solutions which are employed for alleviating nutritional and trace element deficiencies. Nonphytotoxic oils and oil concentrates may also be added.

The following examples are intended to further illustrate the present invention without limiting its scope in any way.

I. Analytics:

Particle sizes were determined by dynamic light scattering with a Malvern Mastersizer 2000 system at 25° C.

Viscosities were measured in analogy to DIN EN ISO 255 with a Brookfield DV-E Viscometer, spindle 1 of the RV spindle set at 50 m$^{-1}$. Alternatively or in addition dynamic viscosities were determined in analogy to OECD Test Guideline 114 ("Viscosity of Liquids").

The pH values of the formulations were determined according to the test method of the Collaborative International Pesticides Analytical Council CIPAC MT 75.3.

Measurements were carried out with 1% (v/v) solutions of the aqueous suspension concentrate formulations in "water D" as defined by CIPAC.

II. Ingredients:

| | |
|---|---|
| Surfactant N1: | blockcopolymer of ethylene oxide and propylene oxide, $M_N$ 6500, EO/PO ratio 50:50 - Pluronic ® PE 10500 (BASF SE) |
| Surfactant N2: | blockcopolymer of ethylene oxide and propylene oxide, $M_N$ 2900, EO/PO ratio 40:60 - Pluronic ® PE 6400 (BASF SE) |
| Surfactant N3: | reaction product of polyethylenimine with 12-hydroxyloctadecanoic acid formulated in kerosene (30 - 60%(v/v)) - Terspersee ® 4890 (Huntsman) |
| Surfactant N4: | poly-ethoxy-co-propoxylated butanol - Atlas G 5000 (Croda) |
| Surfactant N5: | polyethoxylated sorbitol hexaoleate - Atlas G 1086 (Croda) |
| Surfactant A: | sodium salt of a phenolsulfonic acid-formaldehyde polycondensate - Vultamol ® DN (BASF SE) |
| Antifoam Agent: | polydimethylsiloxane emulsion - Silicone SRE-PFL (Wacker) |
| Inorganic Dispersant: | silica - Sipernat ® 22 (Evonik) |
| Thickener: | Xanthan Gum - Kelzan ® (Kelco) |
| Preservative: | 1,2-benzisothiazolin-3-one - Acticide ® MBS (Thor Chemie) |
| Adjuvant 1: | mixture of hydrocarbons and surfactants - Atplus 411 (ICI) |

III. Preparation of the Compositions of the Invention:

General Procedure:

For each Example listed in table 3 all surfactants given, glyphosate in the form specified, saflufenacil anhydrate, a small portion of the antifoam agent and, if applicable, the inorganic dispersant were added to the water or the mixture of water and 1,2-propylene glycol. In case a thickener is to be included in the composition only about 60 to 90% of the volume of water or of the mixture of water and 1,2-propylene glycol were used. The suspension was dispersed using a high shear mixer until homogeneity was reached. The thus obtained slurry was then passed through a bead mill (Dyno mill KDL) until a particle size of below 2 µm for at least 80% by weight of the saflufenacil was achieved. Afterwards, if applicable, a blend of the thickener with the remaining water or water/propylene glycol mixture was added to the suspension and agitation was continued until homogeneity was reached. The preservative was then added and after further agitation also the remaining antifoam Agent. The resulting mixture was stirred for not more than 3 minutes and, if necessary, the pH value of the obtained composition was adjusted with diluted aqueous acetic acid (0.2 g/L).

TABLE 3

| Components | Example | | | | | | | | | |
|---|---|---|---|---|---|---|---|---|---|---|
| | 1 | 2 | 3 | 4 | 5 | 6 | 7 | 8 | 9 | 10 |
| Saflufenacil anhydrate [g] | 28 | 28 | 28 | 28 | 28 | 28 | 28 | 28 | 28 | 28 |
| Glyphosate, acid form [g] | 336 | 336 | 336 | 336 | — | 336 | 336 | 336 | 336 | — |
| Glyphosate, isopropyl-ammonium salt [g] * | — | — | — | — | 336 | — | — | — | — | 336 |
| 1,2-propylene glycol [g] | — | 70 | 70 | 70 | 3.9 | 70 | 70 | 70 | 70 | 3.9 |
| Surfactant N1 [g] | — | — | 14 | — | 1.7 | 30 | 30 | — | — | 1.7 |
| Surfactant N2 [g] | 150 | 150 | — | — | 150 | — | — | 150 | 150 | 150 |
| Surfactant N3 [g] | — | — | 40 | 20 | — | 40 | 20 | 30 | — | — |
| Surfactant N4 [g] | — | — | — | 75 | — | — | — | 75 | — | — |
| Surfactant N5 [g] | 75 | 75 | 75 | 75 | 75 | — | 75 | — | 75 | 75 |
| Surfactant A [g] | — | — | — | — | 1.1 | 40 | — | — | — | 1.1 |
| Antifoam Agent [g] | 5 | 5 | 5 | 5 | 5 | 5 | 5 | 5 | 5 | 5 |
| Inorganic Dispersant [g] | — | — | — | — | 0.3 | — | — | — | — | 0.3 |
| Thickener [g] | — | 2 | 2 | 2 | 2 | — | 2 | 2 | 2 | 1 |
| Preservative [g] | 2 | 2 | 2 | 2 | 2 | 2 | 2 | 2 | 2 | 2 |
| pH | n.d. | 2.6 | 3.0 | n.d. | n.d. | n.d. | 3.0 | 2.6 | 2.7 | n.d. |
| Water | 431 | 422 | 509 | 504 | 409 | 448 | 509 | 398 | 420 | 409 |

* calculated as glyphosate acid form

IV. Storage Stability

A sample of a freshly prepared formulation and samples of formulations that were stored at 20° C., 30° C., 40° C. and 50° C., respectively, for periods of 1, 2, 3, 6 and 12 month at each of the temperatures were taken. In order to investigate the stability of the formulation after these storage conditions, each sample was analyzed regarding the following parameters: percent by weight of particle sizes below 2 μm, viscosity, phase separation or supernatant formation, dispersion stability, saflufenacil content and the pH value. For determining the dispersion stabilities, at first, each sample was diluted to concentrations used in spray liquors. The resulting dispersions were stored for 2 hours at 20° C. and afterwards the volumes of the sediments that may have formed were measured.

In addition to storing at the above indicated temperatures samples of a freshly prepared formulation and samples after storage for 1 month were subjected to 56 freeze-thaw cycles between either −10° C. and +10° C. or −5° C. and +30° C. Afterwards the samples were examined with the same analysis protocol described above.

The results of these analyses of the formulations prepared according to Examples 1 and 2 are summarized in tables 4 to 15 below. In conclusion, in respect to all parameters examined both formulations exhibited good to excellent storage stabilities in a temperature range of at least 20 to 40° C. for at least 6 month. At 50° C. the formulations are at least 3 month sufficiently stable. Moreover, according to the data obtained the formulations remained almost unchanged and showed nearly complete stability during the freeze-thaw cycles detailed above.

TABLE 4

Formulation of Example 1: Suspended saflufenacil with particle sizes below 2 μm in % by weight, based on total amount of saflufenacil

| Storage time [month] | Temperature | | | | | |
|---|---|---|---|---|---|---|
| | 20° C. | 30° C. | 40° C. | 50° C. | −10/+10° C. | −5/+30° C. |
| 0 | 81 | 81 | 81 | 81 | 81 | 81 |
| 1 | 80 | 81 | 80 | 80 | 80 | 81 |
| 6 | 78 | 77 | 77 | 74 | — | — |
| 12 | 75 | 81 | 79 | 73 | — | — |

TABLE 5

Formulation of Example 1: Viscosity [mPa · s] D100 s$^{-1}$ at 20° C.

| Storage time [month] | Temperature | | | | | |
|---|---|---|---|---|---|---|
| | 20° C. | 30° C. | 40° C. | 50° C. | −10/+10° C. | −5/+30° C. |
| 0 | 86 | 86 | 86 | 86 | 86 | 86 |
| 6 | 76 | 71 | 74 | 71 | — | — |

TABLE 6

Formulation of Example 1: Supernatant formed in % by weight

| Storage time [month] | Temperature | | | | | |
|---|---|---|---|---|---|---|
| | 20° C. | 30° C. | 40° C. | 50° C. | −10/+10° C. | −5/+30° C. |
| 0 | 0 | 0 | 0 | 0 | 0 | 0 |
| 1 | 0 | 0 | 0 | 0 | — | — |

TABLE 6-continued

Formulation of Example 1: Supernatant formed in % by weight

| Storage time [month] | Temperature | | | | | |
|---|---|---|---|---|---|---|
| | 20° C. | 30° C. | 40° C. | 50° C. | −10/+10° C. | −5/+30° C. |
| 6 | 0 | 2 | 11 | 38 | — | — |
| 12 | 0 | 14 | 43 | 48 | — | — |

TABLE 7

Formulation of Example 1: Stability of dispersion measured based on volume of sediment formed [ml] after 2 hours

| Storage time [month] | Temperature | | | | | |
|---|---|---|---|---|---|---|
| | 20° C. | 30° C. | 40° C. | 50° C. | −10/+10° C. | −5/+30° C. |
| 0 | 0.00 | 0.00 | 0.00 | 0.00 | 0.00 | 0.00 |
| 1 | 0.00 | 0.00 | 0.00 | 0.00 | — | — |
| 3 | 0.00 | 0.00 | 0.00 | 0.00 | — | — |
| 6 | 0.00 | 0.00 | 0.00 | 0.00 | — | — |
| 12 | 0.00 | 0.00 | 0.00 | 0.00 | — | — |

TABLE 8

Formulation of Example 1: Saflufenacil content in % by weight, based on weight of originally employed safluenacil

| Storage time [month] | Temperature | | | | | |
|---|---|---|---|---|---|---|
| | 20° C. | 30° C. | 40° C. | 50° C. | −10/+10° C. | −5/+30° C. |
| 0 | 100.00 | 100.00 | 100.00 | 100.00 | 100.00 | 100.00 |
| 1 | 100.00 | 100.40 | 98.00 | 98.50 | — | — |
| 3 | 100.00 | 97.10 | 99.00 | 98.30 | — | — |
| 6 | 102.00 | 101.10 | 100.20 | 97.50 | — | — |

TABLE 9

Formulation of Example 1: pH value

| Storage time [month] | Temperature | | | | | |
|---|---|---|---|---|---|---|
| | 20° C. | 30° C. | 40° C. | 50° C. | −10/+10° C. | −5/+30° C. |
| 0 | 4.20 | 4.20 | 4.20 | 4.20 | 4.20 | 4.20 |
| 1 | 4.20 | 4.30 | 4.30 | 4.60 | 4.20 | 4.20 |
| 6 | 4.20 | 4.30 | 4.60 | 5.40 | — | — |
| 12 | 4.30 | 4.40 | 4.90 | 6.10 | — | — |

TABLE 10

Formulation of Example 2: Suspended saflufenacil with particle sizes below 2 μm in % by weight, based on total amount of saflufenacil

| Storage time [month] | Temperature | | | | | |
|---|---|---|---|---|---|---|
| | 20° C. | 30° C. | 40° C. | 50° C. | −10/+10° C. | −5/+30° C. |
| 0 | 80 | 80 | 80 | 80 | 80 | 80 |
| 1 | 58 | 80 | 79 | 79 | 80 | 78 |
| 3 | 79 | 79 | 77 | 76 | — | — |
| 6 | 69 | 74 | 74 | 71 | — | — |
| 12 | 78 | 78 | 78 | 70 | — | — |

TABLE 11

Formulation of Example 2: Viscosity [mPa · s] D100 s$^{-1}$ at 20° C.

| Storage time [month] | Temperature | | | | | |
|---|---|---|---|---|---|---|
| | 20° C. | 30° C. | 40° C. | 50° C. | −10/+10° C. | −5/+30° C. |
| 0 | 87 | 87 | 87 | 87 | 87 | 87 |
| 1 | 78 | 76 | 98 | 75 | 79 | 78 |
| 3 | 85 | 82 | 109 | 81 | — | — |
| 6 | 84 | 81 | 105 | 78 | — | — |
| 12 | 83 | 81 | 106 | 76 | — | — |

TABLE 12

Formulation of Example 2: Supernatant formed in % by weight

| Storage time [month] | Temperature | | | | | |
|---|---|---|---|---|---|---|
| | 20° C. | 30° C. | 40° C. | 50° C. | −10/+10° C. | −5/+30° C. |
| 0 | 0 | 0 | 0 | 0 | 0 | 0 |
| 1 | 0 | 0 | 0 | 2 | 0 | 0 |
| 3 | 0 | 0 | 0 | 0 | — | — |
| 6 | 0 | 0 | 0 | 16 | — | — |
| 12 | 0 | 1 | 8 | 38 | — | — |

TABLE 13

Formulation of Example 2: Stability of dispersion measured based on volume of sediment formed [ml] after 2 hours

| Storage time [month] | Temperature | | | | | |
|---|---|---|---|---|---|---|
| | 20° C. | 30° C. | 40° C. | 50° C. | −10/+10° C. | −5/+30° C. |
| 0 | 0.00 | 0.00 | 0.00 | 0.00 | 0.00 | 0.00 |
| 1 | 0.00 | 0.00 | 0.00 | 0.00 | — | — |
| 3 | 0.00 | 0.00 | 0.00 | 0.00 | — | — |
| 6 | 0.00 | 0.00 | 0.00 | 0.00 | — | — |
| 12 | 0.00 | 0.00 | 0.00 | 0.05 | — | — |

TABLE 14

Formulation of Example 2: Saflufenacil content in % by weight, based on weight of originally employed safluenacil

| Storage time [month] | Temperature | | | | | |
|---|---|---|---|---|---|---|
| | 20° C. | 30° C. | 40° C. | 50° C. | −10/+10° C. | −5/+30° C. |
| 0 | 100.00 | 100.00 | 100.00 | 100.00 | 100.00 | 100.00 |
| 1 | 98.10 | 98.10 | 107.10 | 97.10 | — | — |
| 3 | 98.80 | 98.60 | 107.90 | 98.20 | — | — |
| 6 | 97.80 | 96.20 | 107.90 | 99.30 | — | — |
| 12 | 97.60 | 96.90 | 107.4 | 96.60 | — | — |

TABLE 15

Formulation of Example 2: pH value

| Storage time [month] | Temperature | | | | | |
|---|---|---|---|---|---|---|
| | 20° C. | 30° C. | 40° C. | 50° C. | −10/+10° C. | −5/+30° C. |
| 0 | 4.90 | 4.90 | 4.90 | 4.90 | 4.90 | 4.90 |
| 1 | 4.80 | 4.90 | 5.00 | 5.60 | 4.80 | 4.80 |
| 3 | 4.90 | 5.00 | 5.30 | 6.30 | — | — |
| 6 | 4.90 | 5.10 | 5.90 | 6.50 | — | — |
| 12 | 4.90 | 5.20 | 6.30 | 6.40 | — | — |

V. Herbicidal Activity

The herbicidal activity of the aqueous suspension concentrate formulations according to the invention against various undesirable plants was demonstrated by the following post-emergence treatment field trials.

The test plants listed below were first grown, depending on the plant habit, to a height of 3 to 20 cm. Only then they were treated in parallel with spray liquors prepared from either the formulation according to Example 7, Example 8, Example 9 or Example 10 of the present invention. In all cases the spray liquors were prepared by diluting with water to levels customary for saflufenacil and glyphosate and afterwards adding Adjuvant 1 in such amounts that application rates of 2 L/ha would be obtained. The test plants were sprayed using finely distributing nozzles to the extent that the application rates of saflufenacil and glyphosate given in table 16 were reached.

The test period extended over 21 days. During this time, the plants were tended, and their response to the treatments with active compound was evaluated.

The evaluation for the damage caused by the chemical compositions was carried out using a scale from 0 to 100%, compared to the untreated control plants. Here, 0 means no damage and 100 means complete destruction of the plants.

The plants used in the field trials belonged to the following species:

| Scientific Name | Code | Common Name |
|---|---|---|
| *Alopecurus myosuroides* | ALOMY | slender meadow foxtail |
| *Capsella bursa-pastoris* | CAPBP | shepherd's-purse |
| *Lolium perenne* | LOLPE | perennial ryegrass |
| *Matricaria inodora* | MATIN | corn chamomile |
| *Papaver rhoeas* | PAPRH | corn poppy |
| *Triticum aestivum* | TRZAW | common wheat |
| *Veronica persica* | VERPE | persian speedwell |

Table 16 relates to the herbicidal activity of saflufenacil assessed 21 days after treatment (DAT).

TABLE 16

Application in post-emergence of spray liquors prepared from the aqueous suspension concentrates of Examples 7, 8, 9 and 10

| | application rates [g/ha] | | observed herbicidal activity [%] | | | |
|---|---|---|---|---|---|---|
| Weed | glyphosate | saflu-fenacil | Example 7 | Example 8 | Example 9 | Example 10 |
| ALOMY | 302 | 26 | 95 | 97 | 95 | 92 |
| ALOMY | 604 | 52 | 100 | 100 | 100 | 99 |
| CAPBP | 302 | 26 | 99 | 100 | 100 | 99 |
| CAPBP | 604 | 52 | 100 | 100 | 100 | 100 |
| LOLPE | 302 | 26 | 53 | 52 | 52 | 53 |
| LOLPE | 604 | 52 | 68 | 70 | 68 | 73 |
| MATIN | 302 | 26 | 99 | 99 | 98 | 99 |
| MATIN | 604 | 52 | 100 | 100 | 100 | 100 |
| PAPRH | 302 | 26 | 97 | 100 | 100 | 100 |

TABLE 16-continued

Application in post-emergence of spray liquors prepared from the aqueous suspension concentrates of Examples 7, 8, 9 and 10

| Weed | application rates [g/ha] | | observed herbicidal activity [%] | | | |
|---|---|---|---|---|---|---|
| | glyphosate | saflufenacil | Example 7 | Example 8 | Example 9 | Example 10 |
| PAPRH | 604 | 52 | 100 | 100 | 100 | 100 |
| TRZAW | 302 | 26 | 86 | 88 | 85 | 83 |
| TRZAW | 604 | 52 | 98 | 99 | 98 | 99 |
| VERPE | 302 | 26 | 100 | 95 | 100 | 100 |
| VERPE | 604 | 52 | 100 | 100 | 100 | 100 |

As can be seen from table 16 the formulations according to the invention show high herbicidal activities against a variety of weed targets already 21 days after treatment.

The invention claimed is:

1. An aqueous concentrate formulation for plant protection, comprising:
    a) 2-chloro-5-[3,6-dihydro-3-methyl-2,6-dioxo-4-(trifluoromethyl)-1-(2H)pyrimidinyl]-4-fluoro-N-[[methyl(1-methylethyl)amino]sulfonyl]benzamide in the form of its anhydrate;
    b) N-(phosphonomethyl)glycine in the form of its free acid, in the form of the ammonium salt or a substituted ammonium salt or a mixture thereof;
    c) at least two different non-ionic surfactants with at least one of them comprising an ethylene oxide polymer moiety or an ethylene oxide/$C_3$-$C_4$-alkylene oxide block copolymer moiety, and
    d) water;
wherein the pH-value of the formulation is below 6.

2. The aqueous concentrate formulation of claim 1, wherein the component b) is selected from the group consisting of N-(phosphonomethyl)glycine in the form of its free acid, N-(phosphonomethyl)glycine in the form of the isopropylammonium salt and mixtures thereof.

3. The aqueous concentrate formulation of claims 1, wherein the pH value is 2 to 5.

4. The aqueous concentrate formulation of claim 1, wherein the weight ratio of component a) to component b) is from 1:5 to 1:20.

5. The aqueous concentrate formulation of claim 1, wherein the amount of component b) is from 20 to 45% by weight, based on the total weight of the formulation.

6. The aqueous concentrate formulation of claim 1, wherein the component c) comprises at least one ethylene oxide/$C_3$-$C_4$-alkylene oxide block copolymer.

7. The aqueous concentrate formulation of claim 6, wherein the ethylene oxide/$C_3$-$C_4$-alkylene oxide block copolymer is an ethylene oxide/propylene oxide block copolymer.

8. The aqueous concentrate formulation of claim 6, wherein the amount of the ethylene oxide/$C_3$-$C_4$-alkylene oxide block copolymer is from 1.5 to 20% by weight, based on the total weight of the formulation.

9. The aqueous concentrate formulation of claim 6, wherein the component c) further comprises at least one non-ionic surfactant selected from the group consisting of poly-ethoxy-co-propoxylated $C_3$-$C_{20}$-alkanols, polyethoxylates of esters of polyols with saturated or unsaturated $C_6$-$C_{22}$-alkanoic acids and reaction products of polyethylenimine with an optionally hydroxylated saturated or unsaturated $C_{12}$-$C_{24}$-fatty acid.

10. The aqueous concentrate formulation of claim 9, wherein the component c) comprises at least one ethylene oxide/propylene oxide block copolymer and at least one polyethoxylate of esters of sorbitol with $C_6$-$C_{22}$-alkanoic acids.

11. The aqueous concentrate formulation of claim 9, wherein the component c) comprises an ethylene oxide/propylene oxide block copolymer and the reaction product of polyethylenimine with a hydroxylated saturated $C_{12}$-$C_{24}$-fatty acid.

12. The aqueous concentrate formulation of claim 6 further comprising as a component e) an anionic surfactant selected from the group consisting of $C_1$-$C_{16}$-alkylbenzene sulfonates, $C_1$-$C_{16}$-alkylnaphthaline sulfonates, sulfated polyethoxylates of di- or tristyryl phenol and arylsulfonic acid formaldehyde condensation products.

13. The aqueous concentrate formulation of claim 12, wherein the anionic surfactant is an arylsulfonic acid formaldehyde condensation product.

14. The aqueous concentrate formulation of claim 1, wherein the component c) comprises a poly-ethoxy-co-propoxylated $C_3$-$C_{20}$-alkanol, a polyethoxylate of esters of polyols with $C_6$-$C_{22}$-alkanoic acids and a reaction product of polyethylenimine with a hydroxylated saturated $C_{12}$-$C_{24}$-fatty acid.

15. The aqueous concentrate formulation of claim 1 further comprising as a component f) a water-miscible organic solvent selected from the group consisting of $C_2$-$C_5$-alkane diols and $C_3$-$C_8$-alkane triols.

16. The aqueous concentrate formulation of claim 15, wherein the solvent is propylene glycol.

17. The aqueous concentrate formulation of claim 1 further comprising an inorganic dispersant selected from the group consisting of silicic acid, silica, alumina and calcium carbonate and mixtures thereof.

18. The aqueous concentrate formulation of claim 1 further comprising a thickener selected from the group consisting of silicic acid, layer silicates, organically modified layer silicates, polysaccharides and heteropolysaccharides.

19. The aqueous concentrate formulation of claim 1 comprising:
    from 1 to 10% by weight, based on the total weight of the formulation, of component a);
    from 20 to 45% by weight, based on the total weight of the formulation, of component b);
    from 3 to 30% by weight, based on the total weight of the formulation, of component c); and
    from 15 to 76% by weight, based on the total weight of the formulation, of water.

20. The aqueous concentrate formulation of claim 19 further comprising from 0.1 to 10% by weight, based on the total weight of the formulation, of a solvent selected from the group consisting of $C_2$-$C_5$-alkane diols and $C_3$-$C_8$-alkane triols.

21. A method of controlling undesired vegetation, which comprises applying of the aqueous concentrate formulation of claim 1, in diluted or undiluted form, to plants, their environment and/or on seeds.

* * * * *